(12) United States Patent
Ternes et al.

(10) Patent No.: US 8,352,029 B2
(45) Date of Patent: Jan. 8, 2013

(54) FLEXIBLE NEURAL STIMULATION ENGINE

(75) Inventors: David J. Ternes, Roseville, MN (US); Doug M. Birkholz, Shoreview, MN (US); David W. Yost, Brooklyn Park, MN (US); James A. Esler, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 63 days.

(21) Appl. No.: 12/785,954

(22) Filed: May 24, 2010

(65) Prior Publication Data
US 2010/0234912 A1 Sep. 16, 2010

Related U.S. Application Data

(60) Division of application No. 11/550,912, filed on Oct. 19, 2006, now Pat. No. 7,751,884, which is a continuation-in-part of application No. 11/116,596, filed on Apr. 28, 2005, now Pat. No. 7,769,447.

(51) Int. Cl.
*A61N 1/00* (2006.01)

(52) U.S. Cl. .......................................................... 607/9

(58) Field of Classification Search ........................ 607/9
See application file for complete search history.

(56) References Cited

U.S. PATENT DOCUMENTS

| | | | |
|---|---|---|---|
| 4,378,020 A | 3/1983 | Nappholz et al. |
| 4,407,288 A | 10/1983 | Langer et al. |
| 4,503,857 A | 3/1985 | Boute et al. |
| 4,554,920 A | 11/1985 | Baker, Jr. et al. |
| 4,577,633 A | 3/1986 | Berkovits et al. |
| 4,779,617 A | 10/1988 | Whigham |
| 4,928,688 A | 5/1990 | Mower |
| 5,022,395 A | 6/1991 | Russie |
| 5,081,987 A | 1/1992 | Nigam |
| 5,085,215 A | 2/1992 | Nappholz et al. |
| 5,103,820 A | 4/1992 | Markowitz |
| 5,247,930 A | 9/1993 | Begemann et al. |
| 5,292,340 A | 3/1994 | Crosby et al. |
| 5,312,450 A | 5/1994 | Markowitz |
| 5,360,437 A | 11/1994 | Thompson |
| 5,431,691 A | 7/1995 | Snell et al. |

(Continued)

OTHER PUBLICATIONS

"U.S. Appl. No. 11/116,596, Final Office Action mailed Apr. 7, 2008", 7 pgs.

(Continued)

*Primary Examiner* — Eric D. Bertram
(74) *Attorney, Agent, or Firm* — Schwegman Lundberg & Woessner, P.A.

(57) ABSTRACT

A method for implementing a neural stimulation therapy mode in an implantable medical device (IMD) comprising the acts of mapping respective device states, defined by one or more timer states that include at least one neural event timer or one or more indications of one or more sensed physiologic events, to associated device actions in a stored neural table, storing an event represented as a device status word and a time stamp in a queue in response to an action input, and comparing one or more current timer states or one or more indications of one or more sensed physiologic events to a device state contained in the neural table and, if found to match, causing performance of one or more associated device actions, wherein the device actions include one or more of a neural stimulation energy delivery or a change in one or more timer states.

20 Claims, 9 Drawing Sheets

U.S. PATENT DOCUMENTS

| | | | |
|---|---|---|---|
| 5,545,186 | A | 8/1996 | Olson et al. |
| 5,643,326 | A | 7/1997 | Weiner et al. |
| 5,692,907 | A | 12/1997 | Glassel et al. |
| 5,725,561 | A | 3/1998 | Stroebel et al. |
| 5,776,168 | A | 7/1998 | Gunderson |
| 5,792,203 | A | 8/1998 | Schroeppel |
| 5,991,659 | A | 11/1999 | de Vries et al. |
| 6,026,324 | A | 2/2000 | Carlson |
| 6,129,745 | A | 10/2000 | Sun et al. |
| 6,366,810 | B1 | 4/2002 | Johnson et al. |
| 6,427,084 | B2 | 7/2002 | Baker et al. |
| RE38,119 | E | 5/2003 | Mower |
| 6,920,355 | B2 | 7/2005 | Baker et al. |
| 6,931,282 | B2 * | 8/2005 | Esler .................................. 607/9 |
| 7,006,872 | B2 | 2/2006 | Gielen et al. |
| 7,047,066 | B2 | 5/2006 | Vanderlinde et al. |
| 7,085,952 | B2 | 8/2006 | Huelskamp |
| RE39,897 | E | 10/2007 | Mower |
| 7,643,875 | B2 | 1/2010 | Hiel, Jr. et al. |
| 7,657,312 | B2 | 2/2010 | Pastore et al. |
| 7,751,884 | B2 | 7/2010 | Ternes et al. |
| 7,769,447 | B2 | 8/2010 | Yost et al. |
| 2005/0096705 | A1 | 5/2005 | Pastore et al. |
| 2005/0149128 | A1 | 7/2005 | Heil, Jr. et al. |
| 2006/0247708 | A1 | 11/2006 | Yost et al. |
| 2007/0043398 | A1 | 2/2007 | Ternes et al. |
| 2010/0298900 | A1 | 11/2010 | Yost et al. |

OTHER PUBLICATIONS

"U.S. Appl. No. 11/116,596, Final Office Action Mailed Aug. 28, 2009", 6 pgs.

"U.S. Appl. No. 11/116,596, Non Final Office Action mailed Sep. 24, 2007", 9 pgs.

"U.S. Appl. No. 11/116,596, Non-Final Office Action mailed Jan. 7, 2009", 6 pgs.

"U.S. Appl. No. 11/116,596, Non-Final Office Action mailed Jul. 21, 2008", 8 pgs.

"U.S. Appl. No. 11/116,596, Notice of Allowance mailed Mar. 23, 2010", 6 pgs.

"U.S. Appl. No. 11/116,596, Response filed May 7, 2009 to Non Final Office Action mailed Jan. 7, 2009", 6 pgs.

"U.S. Appl. No. 11/116,596, Response filed Oct. 21, 2008 to Non Final Office Action mailed Jul. 21, 2008", 5 pgs.

"U.S. Appl. No. 11/116,596, Response filed Dec. 26, 2007 to Non-Final Office Action mailed Sep. 24, 2007", 5 pgs.

"U.S. Appl. No. 11/116,596, Response filed Jul. 7, 2008 to Final Office Action mailed Apr. 7, 2008", 5 pgs.

"U.S. Appl. No. 11/116,596, Response filed Jul. 9, 2007 to Restriction Requirement mailed Jun. 7, 2007", 7 pgs.

"U.S. Appl. No. 11/116,596, Restriction Requirement mailed Jun. 7, 2007", 6 pgs.

"U.S. Appl. No. 11/550,912, Examiner Interview Summary mailed Jun. 15, 2009", 2 pgs.

"U.S. Appl. No. 11/550,912, Final Office Action mailed Oct. 1, 2009", 8 pgs.

"U.S. Appl. No. 11/550,912, Non-Final Office Action mailed Mar. 19, 2009", 8 pgs.

"U.S. Appl. No. 11/550,912, Notice of Allowance mailed Feb. 24, 2010", 8 pgs.

"U.S. Appl. No. 11/550,912, Response filed Feb. 23, 2009 to Restriction Requirement mailed Jan. 21, 2009", 9 pgs.

"U.S. Appl. No. 11/550,912, Response filed Jun. 15, 2009 to Non Final Office Action mailed Mar. 19, 2009", 12 pgs.

"U.S. Appl. No. 11/550,912, Response filed Dec. 9, 2009 to Final Office Action mailed Oct. 1, 2009", 12 pgs.

"U.S. Appl. No. 11/550,912, Restriction Requirement mailed Jan. 21, 2009", 6 pgs.

Bakker, P. F., et al., "Beneficial Effects of Biventricular Pacing in Congestive Heart Failure", *PACE*, 17 (4), Part II, NASPE Abstract No. 318, (Apr. 1994), 1 p.

Gaggini, G., et al., "Mixed Microprocessor-Random Logic Approach for Innovative Pacing Systems", *Pacing and Clinical Electrophysiology*, 15 (11), (Nov. 1992), pp. 1858-1861.

Mower, Morton, "", U.S. Appl. No. 10/214,474, filed Aug. 8, 2002, entitled "*Method and Apparatus for Treating Hemodynamic Disfunction*", 3.

Stotts, L. J., et al., "An 8-bit Microcomputer with Analog Subsystems for Implantable Biomedical Application", *IEEE Journal of Solid-State Circuits*, 24 (2), (Apr. 1989), pp. 292-300.

"U.S. Appl. No. 12/848,894, Non-Final Office Action mailed Nov. 1, 2011", 7 pgs.

"U.S. Appl. No. 12/848,894, Final Office Action mailed May 7, 2012", 7 pgs.

"U.S. Appl. No. 12/848,894, Response filed Mar. 1, 2012 to Non-Final Office Action mailed Nov. 1, 2011", 9 pgs.

* cited by examiner

CONDITION WORD

| AVI EXPIRED₁ | VAI EXPIRED₂ | V-SENSE₃ | A-SENSE₄ | PVARP EXPIRED₅ |

ACTION WORD

| V-PACE₁ | A-PACE₂ | RESET AVI₃ | RESET VAI₄ | RESET PVARP₅ |

CONDITION WORD

| AVI EXPIRED 1 | VAI EXPIRED 2 | A SENSE 3 | RV SENSE 4 | LV SENSE 5 | LVPI EXPIRED 6 | CO ≥ ACO 7 |

605

ACTION WORD

| A PACE 1 | RV PACE 2 | LV PACE 3 | RESET AVI 4 | RESET VAI 5 | RESET LVPI 6 | NEURAL PACE 7 |

610

FLEXIBLE NEURAL STIMULATION ENGINE

RELATED APPLICATIONS

This application is a divisional of U.S. patent application Ser. No. 11/550,912, filed Oct. 19, 2006, now issued as U.S. Pat. No. 7,751,884, which is a continuation-in-part of commonly assigned, Yost et al. U.S. patent application Ser. No. 11/116,596, entitled "Cardiac Pacemaker with Table-Based Pacing Mode Implementation," which was filed Apr. 28, 2005, now issued as U.S. Pat. No. 7,769,447, each of which is incorporated by reference herein, and the priority of each of which is claimed herein.

TECHNICAL FIELD

This document pertains generally to the field of cardiac pacemakers, neural stimulators, and implantable cardioverter/defibrillators incorporating a pacing function. In particular, the document relates to the hardware and software used to control the operation of such devices.

BACKGROUND

It is now common for patients having disorders of cardiac rhythm to be treated with implantable pacemakers that provide electrical stimulation to selected chambers of the heart in the form of timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction. Pacing therapy delivered in this manner is referred to as bradycardia or "brady" pacing. Particular bradycardia pacing modes determine how the pacing pulses are delivered in response to sensed cardiac events and lapsed time intervals. Pacing therapy may also be delivered using a bradycardia pacing mode for the purpose of restoring synchronous ventricular contractions in patients with inter-ventricular or intra-ventricular conduction disorders, termed cardiac resynchronization therapy. Other implantable medical devices include devices that provide neural stimulation energy to the patient, implantable diagnostic devices, or implantable drug delivery systems.

The earliest pacemakers were hardware-based devices in which pacing decisions were made by logic circuits implemented in hardware. Most cardiac pacemakers today, however, (including implantable cardioverter/defibrillators with pacing capability) are microprocessor-based systems in which software (a.k.a. firmware, as the term is used here) run by a microprocessor commands the generation of pacing outputs, with various timers being used to alert the microprocessor as to when to pace. Such firmware-based systems exhibit great flexibility, as compared with a pacemaker implemented with dedicated hardware, since the behavior of the device can be changed simply by reprogramming the microprocessor. Controlling the delivery of paces with a firmware-based system, however, also has some disadvantages. If the microprocessor continually executes instructions during the cardiac cycle in order to process and respond to timing and sensing events, a large amount of battery power is consumed. Also, making pacing decisions with software inevitably introduces some variability into the timing of the paces, commonly referred to as pacing jitter.

SUMMARY

In an approach described herein, a bradycardia pacing mode is implemented using a brady table which maps particular device states, as defined by the occurrence of sensed events and the states of timers, to particular device actions such as the delivery of pacing pulses and the resetting or stopping of timers. Hardware-based circuitry compares the current state of the device to the device states contained in the brady table. If the current device state matches a table device state, the circuitry performs the actions to which the table device state is mapped. The brady table may be stored in an area of RAM, referred to as the brady RAM, which can be accessed by a microprocessor as well as the hardware-based circuitry. Device behavior may thus be easily changed by loading a different brady table into the brady RAM.

In certain examples, an implantable medical device (IMD) includes stimulation circuitry adapted to provide neural stimulation energy to a neural stimulation electrode. The IMD also includes one or more timers, including at least one neural event timer, a device behavior memory including a neural table, and a comparison circuit. The neural table maps a particular device state defined at least in part by a neural event timer to one or more associated device actions that include at least one of a neural stimulation energy delivery, a change in state of at least one neural event timer, and both a neural stimulation energy delivery and a change in state of one or more neural event timers. The comparison circuit compares a current state of one or more neural event timers to a device state in the neural table and, if found to match, causes performance of one or more associated device actions.

A method example includes mapping respective device states defined by one or more timer states, including at least one neural event timer, or one or more sensed physiologic events, to associated device actions in a neural table, and comparing one or more current timer states or one or more sensed physiologic events to a device state contained in the neural table and, if found to match, causing performance of one or more associated device actions. The device actions include neural stimulation energy delivery or changes in one or more timer states.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

Figure 1:
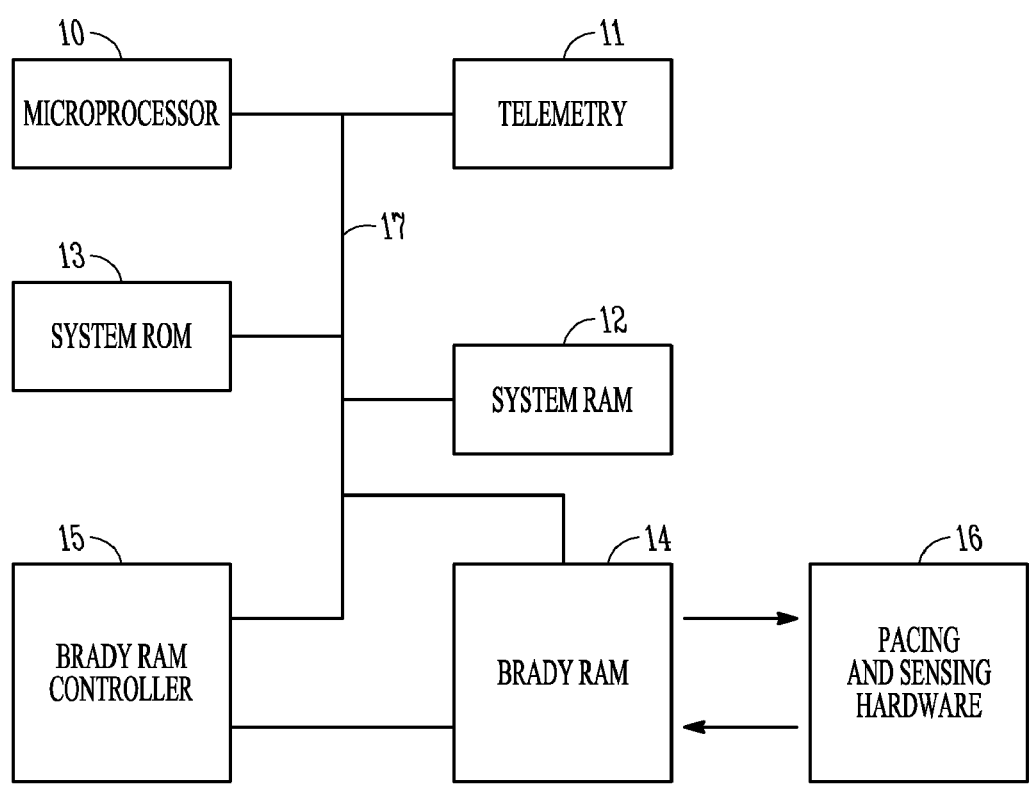
FIG. 1 is a system diagram of an implantable pacemaker.

Described herein is a device and method, such as for implementing a bradycardia pacing mode which allows for a low power implementation that is mostly hardware-based but still allows the flexibility for making major changes in brady behavior normally found only in firmware-based implementations. The brady behavior of the device is encapsulated by a RAM-based table in an area of RAM referred to as brady RAM, and the brady behavior can be changed by re-loading the brady RAM with a different table. Firmware executed by a microprocessor may load the table based on the brady mode desired. Hardware then reads the table only when pacing decisions need to be made, and uses the information in the table to make brady decisions. The design may be easily extended to more complicated pacing modes by making the RAM larger. Because hardware rather than firmware decides when to pace, there is no latency in pace delivery, and no jitter in the cycle length. The device may also utilize a FIFO queue in an area of the brady RAM or elsewhere in which either hardware or firmware may record particular events along with a timestamp for latter retrieval and analysis. The RAM based brady table may be used to define which brady events the hardware will put in a FIFO. Firmware can also place any event in the FIFO, where such events may be unrelated to brady events. The FIFO queue eases the task of keeping events in chronological order when both hardware and firmware are recording events.

Set forth below are descriptions of an example of an implantable device and hardware for implementing a bradycardia pacing mode and a neural stimulation therapy mode in the manner just described. An example of an implementation of a pacing mode using a brady table is also given.

1. Implantable Device Description

An implantable pacemaker includes a housing containing electronic circuitry and one or more electrodes in electrical contact with the myocardium used for sensing and pacing the heart. The housing is usually implanted subcutaneously on the patient's chest, and is usually connected to the electrodes by leads threaded through the vessels of the upper venous system into the heart. The electronic circuitry contained within the housing includes a battery, circuitry for generating pacing pulses, circuitry for interpreting electrogram signals representing cardiac electrical activity, and logic circuitry for operating the pacemaker in a number of programmed pacing modes where a pacing mode defines how pacing pulses are output in response to particular sensed events and the expiration of particular defined time intervals. Telemetry circuitry is usually also provided to enable communication with an external programmer that can interrogate the pacemaker and receive stored data as well as directly adjust the operating parameters of the pacemaker after implantation.

An electrode can be incorporated into a sensing channel that generates an electrogram signal representing cardiac electrical activity at the electrode site and/or incorporated into a pacing channel for delivering pacing pulses to the site. A pacing channel includes a pulse generator connected to an electrode while a sensing channel typically includes a sense amplifier connected to an electrode and a comparator circuit for comparing the electrogram signal to a specified threshold value. The sensing circuitry of the device generates atrial and/or ventricular electrogram signals from the voltages sensed by the electrodes of a particular channel. An electrogram is analogous to a surface EKG and indicates the time course and amplitude of cardiac depolarization and repolarization that occurs during either an intrinsic or paced beat. When an electrogram signal in an atrial or ventricular sensing channel exceeds a specified threshold (e.g., as determined by a comparator) the sensing circuitry detects an atrial or ventricular sense, respectively, which pacing algorithms may employ to trigger or inhibit pacing. Sensing and/or pacing channels may be configured as either atrial or ventricular channels allowing the device to deliver conventional ventricular single-site pacing with or without atrial tracking, biventricular pacing, or multi-site pacing of a single chamber.

2. Bradycardia Pacing Modes

Bradycardia pacing modes are used to pace the atria and/or ventricles in a manner that enforces a certain minimum heart rate or restores AV conduction. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. In a triggered mode, a sense occurring in one heart chamber triggers a pace to either the same or a different heart chamber. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. For example, a ventricular escape interval for pacing the ventricles can be defined between ventricular events, referred to as the cardiac cycle (CC) interval with its inverse being the lower rate limit or LRL. The CC interval is restarted with each ventricular sense or pace. An atrial escape interval can also be defined, for pacing the atria either alone or in addition to pacing the ventricles, which starts with a ventricular sense or pace and is referred to as the ventriculo-atrial interval or VAI. In atrial tracking and AV sequential pacing modes, another ventricular escape interval is defined between atrial and ventricular events, referred to as the atrio-ventricular pacing delay interval or AVI, where a ventricular pacing pulse is delivered upon expiration of the atrio-ventricular pacing delay interval if no ventricular sense occurs before. In an atrial tracking mode, the atrio-ventricular pacing delay interval is triggered by an atrial sense and stopped by a ventricular sense or pace. In an AV sequential pacing mode, the atrio-ventricular delay interval is triggered by an atrial pace and stopped by a ventricular sense or pace. Atrial tracking and AV sequential pacing are commonly combined so that an AVI starts with either an atrial pace or sense.

Cardiac resynchronization therapy is pacing stimulation applied to one or more heart chambers in a manner that compensates for conduction delays, and is most conveniently delivered in conjunction with a bradycardia pacing mode. Ventricular resynchronization pacing is useful in treating heart failure in patients with interventricular or intraventricular conduction defects because, although not directly inotropic, resynchronization results in a more coordinated contraction of the ventricles with improved pumping efficiency and increased cardiac output. Ventricular resynchronization can be achieved in certain patients by pacing at a single unconventional site, such as the left ventricle instead of the right ventricle in patients with left ventricular conduction defects. Resynchronization pacing may also involve biventricular pacing with the paces to right and left ventricles delivered either simultaneously or sequentially, with the interval between the paces termed the biventricular delay (BVD) interval (also sometimes referred to as the VV delay). The BVD interval may be zero in order to pace both ventricles simultaneously, or non-zero in order to pace the left and right ventricles sequentially. In an example biventricular resynchronization pacing mode, right atrial paces and senses trigger an AVI which upon expiration results in a pace to one of the ventricles and which is stopped by a right ventricular sense. The contralateral ventricular pace is delivered at the specified BVD interval with respect to expiration of the AVI.

Another aspect of bradycardia pacing modes involves the use of timer-defined refractory periods for the sensing channels. In order to prevent cross-talk between sensing channels and other types of false sensing, certain events may cause a sensing channel to be rendered refractory for specified period time, during which sensed events may be ignored for purposes of the pacing algorithm, interpreted as noise, or only used for other purposes such as tachyarrhythmia detection. A refractory period is initiated when a particular event starts a timer, which defines the refractory period, and is terminated upon expiration of the timer. Sensing channels are commonly rendered refractory for a period of time upon occurrence of a sense or pace in the same or different channel. One example of a cross-chamber refractory period is the post-ventricular atrial refractory period or PVARP which renders the atrial sensing channel refractory for a period of time following a ventricular sense or pace in order to prevent pacemaker mediated tachycardia.

3. Electronic Circuitry for Implementing Bradycardia Pacing

FIG. 1 is a system diagram of the electronic components contained within the pacemaker housing which are used to implement a pacing mode by causing the delivery of paces in response to sensed cardiac events and lapsed time intervals. A microprocessor 10 communicates with a system RAM 12 and a system ROM 13 for containing data and programmed instructions over a bidirectional system address and data bus 17. Telemetry circuitry 11 is also interfaced to the bus enabling communication between the microprocessor and an external programmer. The microprocessor 10 controls the overall operation of the device in accordance with programmed instructions stored in memory. In most pacemaker designs being used at the present time, instructions executed by a microprocessor are also responsible for implementing the pacing mode by making pacing decisions based on the outputs of timers and sensing circuitry in what may be termed a firmware-based implementation. In the presently described approach, on the other hand, the pacing algorithm is encapsulated by a brady table which maps particular device states, as defined by the occurrence of sensed events and the states of timers, to particular device actions such as the delivery of pacing pulses and the resetting or stopping of timers. Hardware-based circuitry driven by a clock signal compares the current state of the device to the device states contained in the brady table. If the current device state matches a table device state, the circuitry performs the actions to which the table device state is mapped. The brady table may be stored in an area of RAM, referred to as the brady RAM, which can also be accessed by the microprocessor. Device behavior may thus be easily changed by loading a different brady table into the brady RAM. This approach thus obtains the advantages of hardware driven pacing, namely, low power and timing stability, but offers a flexibility similar to that of firmware-based pacing implementations. FIG. 1 illustrates a brady RAM 14 and brady RAM controller 15 interfaced to the bus 17. When enabled by the microprocessor, the brady RAM controller 14 sequentially accesses the table device states and associated actions contained in the brady RAM. The brady RAM 14 is interfaced to pacing and sensing hardware 16 which includes the sensing and pacing channels of the device and hardware timers for defining escape intervals and refractory periods. Logic circuitry associated with the brady RAM 14 includes circuitry for comparing the current state of the device with the table device states and for causing the device actions contained in the brady table to be performed by the hardware 16.

Figure 2:
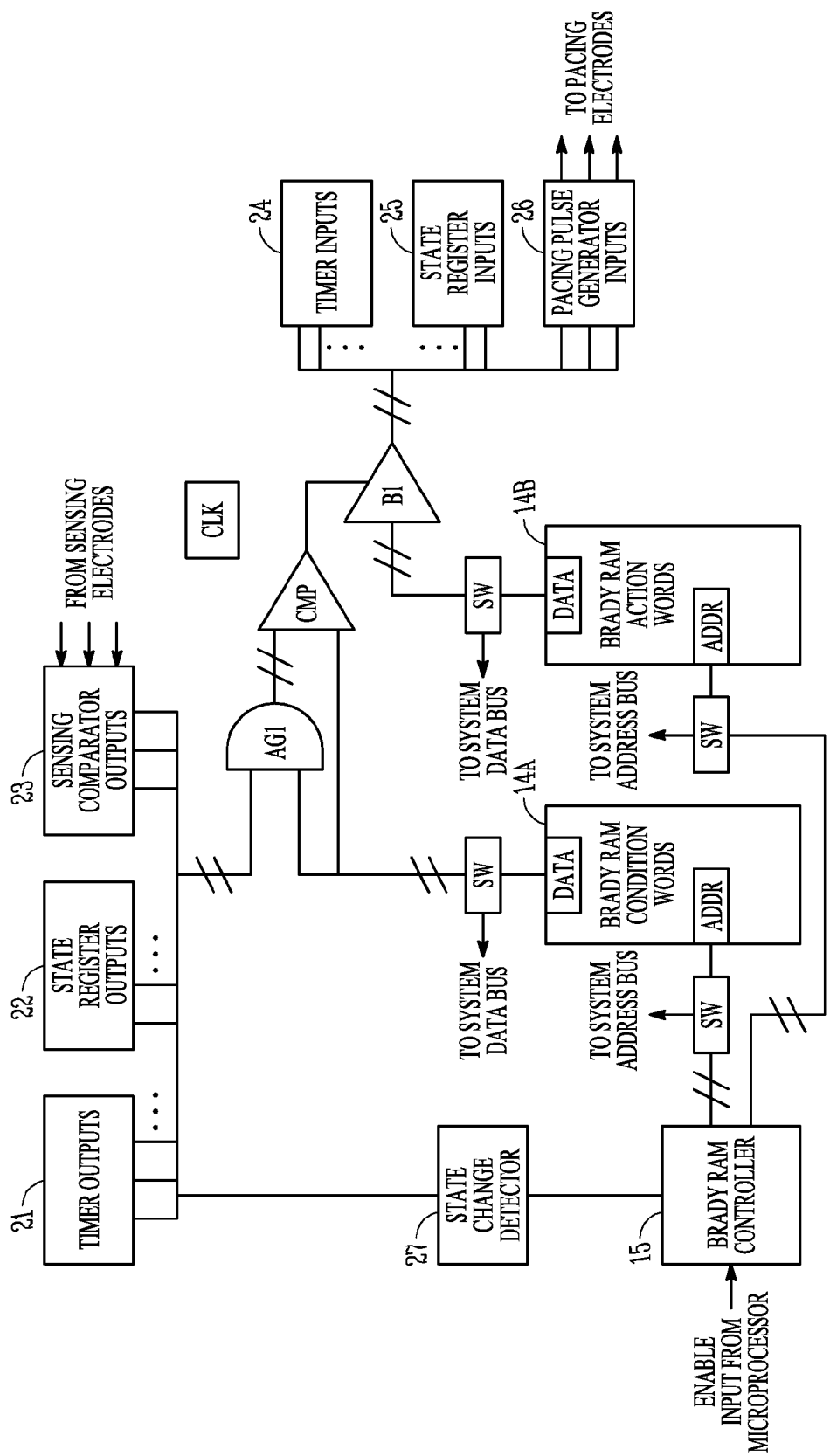
FIG. 2 illustrates hardware for implementing a pacing mode with a brady table.

FIG. 2 illustrates the operation of the brady RAM-based pacing circuitry in more detail according to one particular embodiment. The brady RAM is shown as being divided into a brady RAM 14a which contains a set of condition words and a brady RAM 14b which contains an action word corresponding to each condition word. Each condition word represents a particular device state according to whether particular bits of the word are set or cleared, and each action word represents particular actions which can be performed by the device according to whether particular bits of the word are set or cleared. In certain examples, each bit of a condition word may represent the state of a particular timer or whether a particular sensed event has occurred, and each bit of an action word may represent a timer input or delivery of a pace through a particular pacing channel. When enabled by the microprocessor 10, the brady RAM controller 15 accesses the brady RAM by asserting the address of a condition word to the brady RAM 14a and the address of the corresponding action word to brady RAM 14b. When the brady RAM controller 15 is enabled, the microprocessor also actuates a plurality of solid state switches SW which isolate the brady RAM 14a and 14b from the system address and data bus 17. The switches SW block the system address bus and pass the address outputs of the brady RAM controller to the brady RAM when the brady RAM controller is operating, and vice-versa when the microprocessor 10 is accessing the brady RAM. Similarly, the data bits of both brady RAM 14a and 14b are also isolated from the system data bus 17 by switches SW when the brady RAM controller is operating, and vice-versa when the microprocessor is reading or writing to the brady RAM.

The current state of the device is represented by a set of timer outputs 21 (i.e., timer states such as running, stopped, or expired), a set of state register outputs 22 which may define certain behaviors, and a set of sensing comparator outputs 23. The state register outputs may define any type of detected condition or event which can be used to affect device behavior (e.g., detection of a noisy condition in a particular sensing channel). Together, these outputs may be thought of as a current status word. The condition words in the brady RAM 14a are constructed with a bit-by-bit correspondence to the outputs of the current status word. The actions which may be taken by the device in implementing a bradycardia pacing mode are represented by a set of action inputs which may include timer inputs 24 (e.g., starting or resetting, stopping, or disabling a particular timer), a set of state register inputs 25 which cause the contents of the state registers to change, and a set of pacing pulse generator inputs 26 which cause delivery of paces to particular pacing electrodes. An action input may also be provided for causing a particular event represented in the current status word to be stored in a FIFO queue along with a time stamp. The FIFO queue may be located in the brady RAM or elsewhere. The action words in the brady RAM 14b are constructed with a bit-by-bit correspondence to the set of available action inputs.

The operation of the brady hardware starts when the brady RAM controller 15 is enabled. In this embodiment, the operation of the brady RAM controller is triggered by a change in device status. When a bit of the current status word changes as detected by state change detector 27, the brady RAM controller begins to sequence through each condition word in the brady table by sequentially asserting the address of each condition word to the brady RAM 14a and the address of the corresponding action word to brady RAM 14b. A signal derived from the system clock CLK drives the brady RAM controller at an appropriate frequency to cause the addresses of the condition and actions words to be asserted in sequence. As the address of a condition word is asserted, the data bits of the condition word are output from the brady RAM 14a. In this embodiment, a set bit (i.e., a one) in the condition word signifies a particular timer state or sensing comparator output which defines a particular device state, and a cleared bit (i.e., a zero) signifies that a particular timer state or sensing comparator output does not matter in defining the particular device state. In order to evaluate whether a device state defined by a condition word matches the current device state, the condition word is passed to a multi-bit AND gate AG1 where the condition word is ANDed with the current status word. The output of the gate AG1 is then compared with the condition word by a multi-bit comparator CMP. If the condition word represents the current state of the device, the output of comparator CMP is asserted which enables the multi-bit buffer B1. The data bits of the corresponding action word in the brady RAM 14*b* which are addressed by the brady RAM controller are then passed to the set of action inputs to cause the actions specified by the action word. After all of the condition words are evaluated in this manner, the brady RAM controller waits for another change in the device state and then repeats the sequence.

4. Example Pacing Mode Implementation

The brady RAM-based circuitry described above may be configured to implement any pacing mode where paces are delivered in accordance with defined timer states and sensed events. By way of example, what follows is a description of a simplified atrial and ventricular pacing mode and how that pacing mode is implemented in the brady RAM as condition words and corresponding action words.

Figures 3, 4:
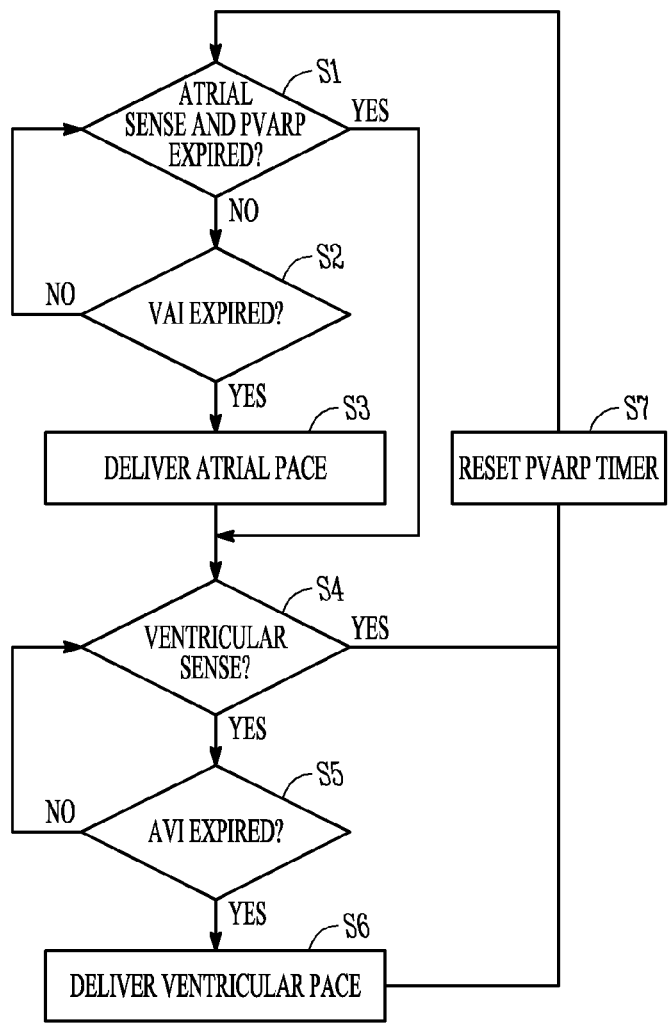
FIG. 3 illustrates an exemplary bradycardia pacing mode.
FIG. 4 illustrates an example of action and condition word construction for a pacemaker.

FIG. 3 illustrates a particular DDD pacing algorithm as steps S1 through S7. Two escape intervals are defined: an AVI started by an atrial sense or pace which upon expiration results in a ventricular pace, and a VAI started by a ventricular sense or pace which upon expiration results in an atrial pace. Only one refractory period is defined, a PVARP, which is started by a ventricular sense or pace and which renders the atrial sensing channel refractory for its duration.

FIG. 4 shows how the timer states, sensed events, and device actions of the pacing algorithm illustrated by FIG. 3 are encoded as condition words and action words. A condition word has five bits numbered 1 through 5 which, if set, represent AVI expiration, VAI expiration, a ventricular sense, an atrial sense, and PVARP expiration, respectively. An action word also has five bits numbered 1 through 5 which, if set, represent a ventricular pace, an atrial pace, resetting (i.e., restarting) the AVI, resetting the VAI, and resetting the PVARP, respectively.

Figure 5:
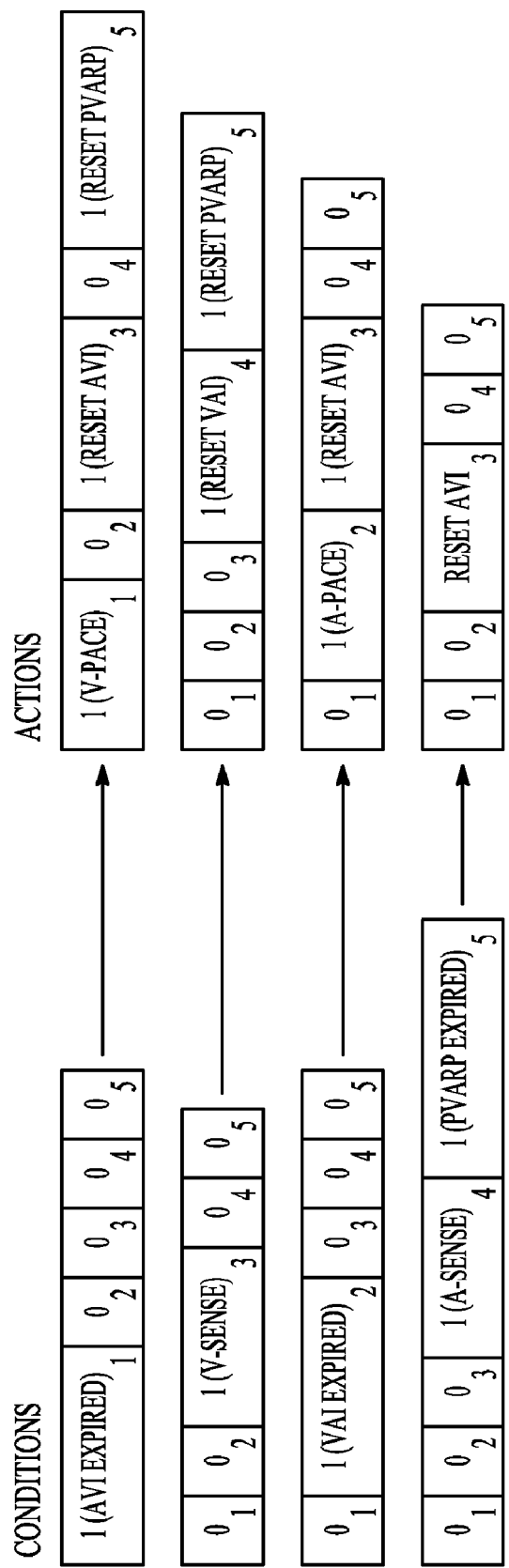
FIG. 5 illustrates exemplary action and condition word pairs for implementing a bradycardia pacing mode.

FIG. 5 shows how different condition words may be associated with different action words in a brady table in order to implement the pacing algorithm illustrated by FIG. 3. The implementation requires four condition/action word pairs which map different device states to different device actions. The first pair results in a ventricular pace being delivered if the AVI is expired regardless of what else is included in the current status word. The VAI and PVARP are also reset. The second pair causes resetting of the VAI and PVARP when a ventricular sense occurs. The third pair causes delivery of an atrial pace and resetting of the AVI when the VAI expires. The fourth pair shows that an atrial sense causes resetting of the AVI only if the PVARP is also expired. This latter behavior may alternatively be interpreted as not generating an atrial sense if the PVARP is unexpired.

5. Implantable Neural Stimulator

Neural stimulation refers to the stimulation of nerve bundles in various regions of the body using electrical energy. Implantable medical devices capable of providing neural stimulation may be useful for several reasons.

For example, ventricular remodeling includes one or more alterations in cardiac cellular structure, such as can result from hypertrophy of the ventricular myocardium due to increased pressure-volume in the ventricles due to a compensatory mechanism in heart failure patients. Although ventricular dilation and hypertrophy may at first be compensatory and increase cardiac output, the processes eventually result in both systolic and diastolic dysfunction. The extent of ventricular remodeling is believed positively correlated with increased mortality in CHF patients.

Examples of methods and devices for delivering multi-site ventricular pacing therapy in conjunction with stimulation of parasympathetic nerves innervating the heart are described in Pastore et al., U.S. Pat. Application Publication No. 20050096705, entitled "Multi-site Ventricular Pacing Therapy with Parasympathetic Stimulation," filed Nov. 3, 2003, now issued as U.S. Pat. No. 7,657,312, which is incorporated herein by reference. Stimulation of cardiac parasympathetic nerves decreases myocardial contractility. Such parasympathetic stimulation acts to decrease the stresses experienced by the ventricular walls during systole so as to decrease, prevent, or reverse the cardiac remodeling that can occur in heart failure patients. The parasympathetic stimulation may be delivered by an implantable cardiac device via a bipolar electrode incorporated into a lead adapted for transvenous insertion, such as into the superior or inferior vena cava. In order to counteract a tendency of parasympathetic stimulation to reduce cardiac output, the delivery of parasympathetic stimulation may be modulated in accordance with the patient's exertion level and/or a sensed parameter related to cardiac output. The device measures the patient's exertion level with a minute ventilation sensor or an accelerometer and delivers parasympathetic stimulation only when the measured exertion level is below a specified limit value.

Another example of a neural stimulation therapy relates to hypertension. Hypertension is a cause of heart disease and other related cardiac co-morbidities. Hypertension occurs when blood vessels constrict. As a result, the heart works harder to maintain flow at a higher blood pressure, which can contribute to heart failure. A pressoreceptive region or field is capable of sensing changes in pressure, such as changes in blood pressure. Pressoreceptor regions can include baroreceptors, which generally include any sensors of pressure changes. For example, baroreceptors can include afferent nerves and can further include sensory nerve endings that are sensitive to the stretching of the wall that results from increased blood pressure from within, and that function as the receptor of a central reflex mechanism that tends to reduce the pressure. Baroreflex functions as a negative feedback system, and relates to a reflex mechanism triggered by stimulation of a baroreceptor. Increased pressure stretches blood vessels, which in turn activates baroreceptors in the vessel walls.

Activation of baroreceptors naturally occurs through internal pressure and stretching of the arterial wall, causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance. Direct electrical stimulation of parasympathetic nerves can activate the baroreflex, inducing a reduction of sympathetic nerve activity and reducing blood pressure by decreasing vascular resistance. Examples of systems and methods to treat hypertension using neural stimulation energy are described in Heil et al., U.S. Pat. Application Publication No. 20050149128, entitled "Baroreflex Stimulation System to Reduce Hypertension," filed Dec. 24, 2003, now issued as U.S. Pat. No. 7,643,875, which is incorporated herein by reference.

6. Example of Neural Stimulator Mode Implementation

A neural stimulation device can be implemented as an implantable medical device (IMD). The neural stimulation behavior of the IMD can be included in a RAM-based table in an area of RAM referred to as device behavior RAM, and the neural stimulation behavior can be changed by re-loading the device behavior RAM with a different table, which can be referred to as a neural table. Firmware executed by a processor may load the table based on the neural stimulation mode desired. For example, firmware may be loaded that only provides timed neural stimulation, or firmware may be loaded that provides neural stimulation in accordance with a patient's sensed exertion level. The firmware is typically executed on a digital signal processor, ASIC, microprocessor, or other type of processor. Hardware then need only read the neural table when one or more neural stimulation decisions need to be made using the information in the neural table.

Figure 6:
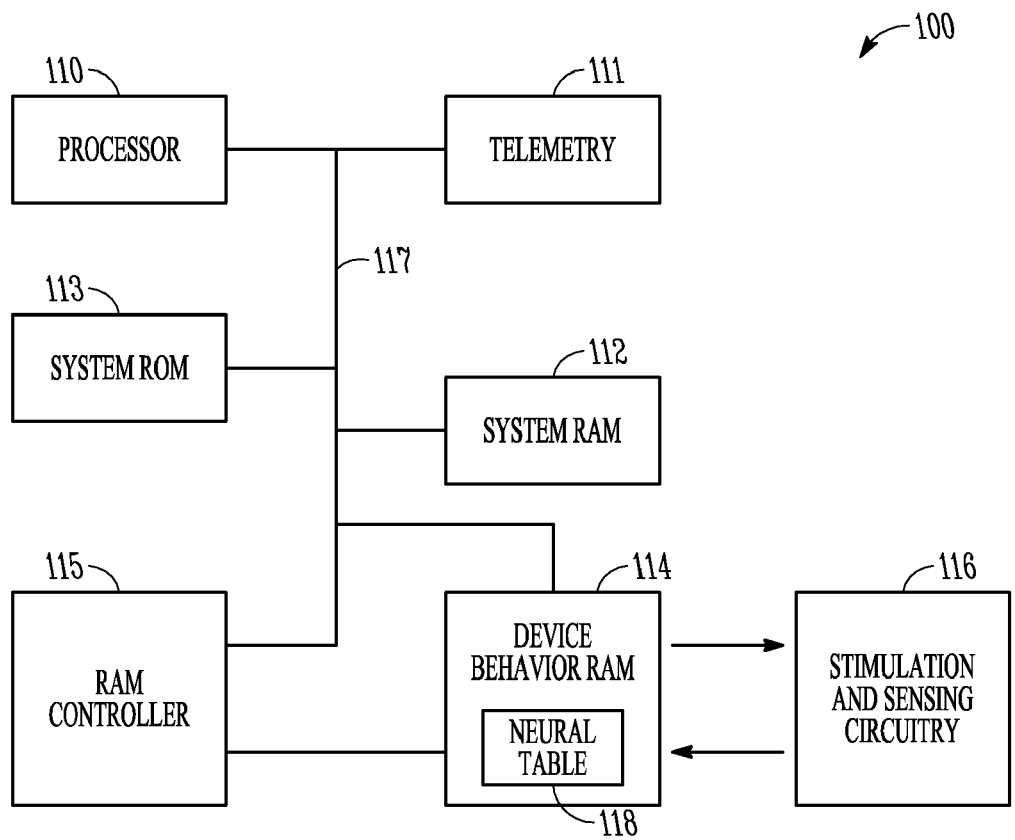
FIG. 6 is a system diagram of an implantable neural stimulation device.

FIG. 6 is a system block diagram showing a portion of an example of electronic components contained within an IMD 100. The electronic components include neural stimulation circuitry 116 to deliver neural stimulation energy to at least one neural stimulation electrode in response to at least one of one or more sensed physiologic events and one or more lapsed time intervals.

A processor 110 communicates with a system RAM 112 and a system ROM 113 for containing data and programmed instructions. Such communication typically takes place over a bidirectional system address and data bus 117. Telemetry circuitry 111 is also interfaced to the bus 117, such as for enabling communication between the processor 110 and an external programmer. The processor 110 controls the overall operation of the IMD 100 in accordance with programmed instructions stored in memory. The IMD 100 also includes one or more timers including at least one neural event timer to time one or more durations between neural events. An example of a neural event timer is a neural escape timer, where neural stimulation energy is delivered if the neural escape timer expires without being reset, such as by an occurrence of a sensed event. For example, if the sensed exertion level drops below a predetermined exertion level threshold. One or more neural event timers can be implemented in the processor 110 or in one or more separate logic circuits. A timer generally includes an output indicating a timer state and an input for changing the timer state.

In some examples, the IMD 100 also includes one or more implantable sensors, which typically produce an electrical sensor signal related to one or more physiologic events of a subject. Examples of implantable sensors include a heart sound sensor, a blood pressure sensor, an intrinsic cardiac signal sensing circuit adapted to sense one or more intracardiac electrograms, a subcutaneous electrocardiograph (ECG) sensing circuit, a cardiac wall motion sensor, a transthoracic impedance sensor, an intracardiac impedance sensor, an accelerometer, and a temperature sensor. The one or more implantable sensors are coupled to sensing circuitry. The sensing circuitry produces an indication of a sensed physiologic event, such as when the electrical sensor signal exceeds a specified threshold value, or when the electrical sensor signal differs from a specified threshold value by a specified amount.

The neural stimulation algorithm is generally contained in a neural table 118 in a device behavior RAM 114. The neural table 118 maps particular device states to particular device actions, such as the delivery of neural stimulation energy or the resetting or stopping of one or more timers. Device states are defined by at least one of the state of one or more timers, including a neural event timer, and the occurrence of one or more sensed physiologic events. In some examples, the sensing circuitry 116 includes one or more comparators, and the one or more outputs of the one or more comparators are included in a device state. In some examples, the IMD 100 further includes one or more state registers used to define device behavior. A comparison circuit can include hardware-based circuitry driven by a clock signal to compare the current state of the IMD 100 to the device states contained in the neural table 118. If the current device state matches a particular table device state, then the circuitry performs the one or more actions to which that particular table device state is mapped. Device actions may include a neural stimulation energy delivery, a change in state of at least one neural event timer, or both a neural stimulation energy delivery and a change in state of a neural event timer. Device behavior is easily changed by loading a different neural table 118 into the device behavior RAM 114.

In some examples, the IMD 100 includes a RAM controller 115 interfaced to the bus 117. When enabled by the microprocessor, the RAM controller 115 sequentially accesses the neural table device states and associated actions contained in the device behavior RAM 114. The device behavior RAM 114 is interfaced to stimulation and sensing circuitry 116 which includes the sensing and neural stimulation channels of the IMD 100 and may include one or more hardware timers. Logic circuitry associated with the device behavior RAM 114 may include the comparison circuit for comparing the current state of the device with the table device states and for causing the device actions contained in the neural table 118 to be performed by the stimulation and sensing circuitry 116.

The state of the IMD 100 may be represented by a set of timer outputs, or a set of state register outputs, or a set of sensing circuit outputs, or any combinations of timer outputs, state register outputs, and sensing circuit outputs. In some examples, such outputs form a device status word and the current state of the outputs defines the current device status word.

According to some examples, the device behavior RAM 114 includes a set of one or more condition words and a set of one or more action words. A condition word represents a particular device state according to which bits of the condition word are set or cleared. In some examples, the condition words have a bit-by-bit correspondence to a device status word. An action word corresponds to one or more condition words. The action words represent one or more corresponding device actions such as providing neural stimulation energy or changing a state of a timer depending on which bits of the action word are set or cleared. A device action is represented by a set of one or more action inputs, which correspond to inputs of timers or inputs to circuits that cause delivery of neural stimulation energy to at least one neural stimulation electrode. In some examples, an action word has a bit-by-bit correspondence to a set of one or more of the action inputs.

In some examples, the IMD 100 includes a first-in first-out (FIFO) buffer queue that may reside in an area of the device behavior RAM 114 or elsewhere. The FIFO stores device events that can be condition words or action words. The neural table 118 may determine whether a neural event is loaded in a FIFO by the hardware. In some examples, the device includes at least one action input to cause at least one particular event represented in the current status word to be loaded into the FIFO. The event may be a neural event or an event unrelated to neural events, such as a brady event for example or another cardiac event. An event may be placed in the FIFO together with a timestamp for later retrieval and analysis. The FIFO queue is useful to keep hardware and firmware events in chronological order.

As discussed previously, a device state can be represented by a set of outputs and the current state of the outputs can be thought of as defining a current device status word. The operation of the RAM controller 115 is triggered by a change in the device state. In some examples, the IMD 100 includes a state change detector. When one or more bits of the current device status word change and the change is detected by the state change detector, the RAM controller 115 begins to sequence through each condition word in the neural table by sequentially asserting addresses of the condition words in the device behavior RAM 114 and an address of an associated action word if they are addressed separately.

As the address of a condition word is asserted, the data bits of the condition word are output from the device behavior RAM 114. In some examples, a set bit (i.e., a one) in the condition word signifies a particular timer state or sensing circuit output that defines a particular device state, and a cleared bit (i.e., a zero) signifies that a particular timer state or sensing circuit output does not matter in defining the particular device state. In order to determine whether a device state defined by a condition word matches the current device state, the condition word is ANDed with the current status word. The output of the gate AG1 is then compared with the condition word by a multi-bit comparator CMP. If the condition word represents the current state of the device, the data bits of the corresponding action word in the device behavior RAM 114 are then passed to the set of one or more action inputs to cause the one or more actions specified by the action word. In some examples, the one or more action words are loaded into a FIFO and one or more device actions are performed by removing the one or more action words from the FIFO and applying the one or more action words to the one or more action inputs. After all of the condition words are evaluated in this manner, the RAM controller 115 waits for another change in the device state and then repeats the sequence.

Figure 7:
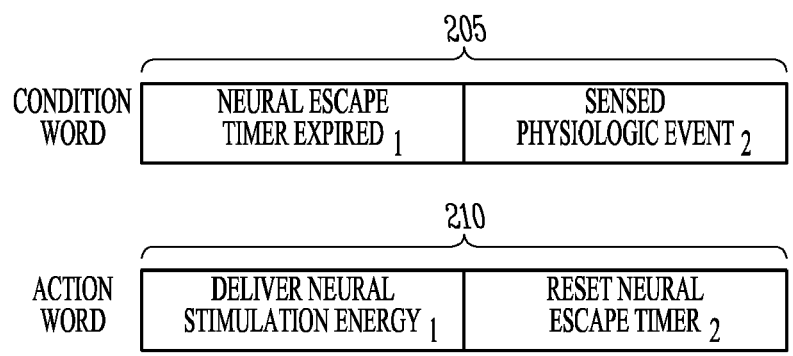
FIG. 7 illustrates an example of action and condition word construction for a neural stimulation device.
Figure 8:
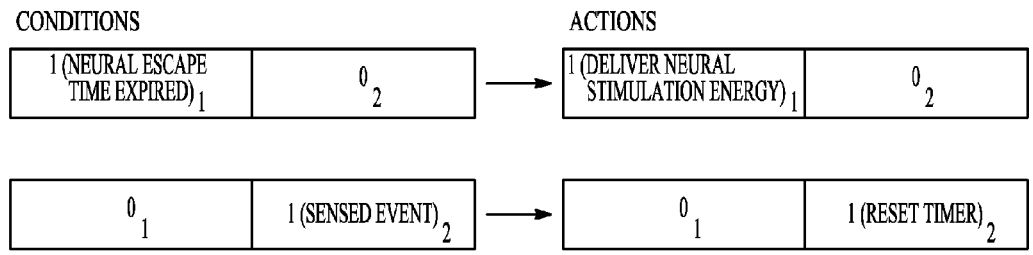
FIG. 8 illustrates exemplary action and condition word pairs for implementing a neural stimulation therapy mode.

FIG. 7 shows a case of how timer states, sensed events, and device actions of an implantable neural stimulation device can be encoded as condition words and action words. A condition word 205 includes a bit representing expiration of a neural escape timer and a bit representing a physiologic event being sensed by the sensing circuitry. An action word 210 includes a bit to enable delivery of neural stimulation energy and a bit to reset a neural escape timer. The neural stimulation energy can be delivered to, among other things, stimulate parasympathetic nerves, activate one or more baroreceptors, or to stimulate the vagus nerve. FIG. 8 shows an association of condition words with the action words. There are two condition/action pairs in this illustrative example. The first pair indicates that neural stimulation energy will be delivered if the neural escape time expires. The second pair indicates that the neural escape timer will be reset if a physiologic event is sensed. The sensed event could be any physiologic event sensed using one or more of the implantable sensors discussed previously.

Figure 9:
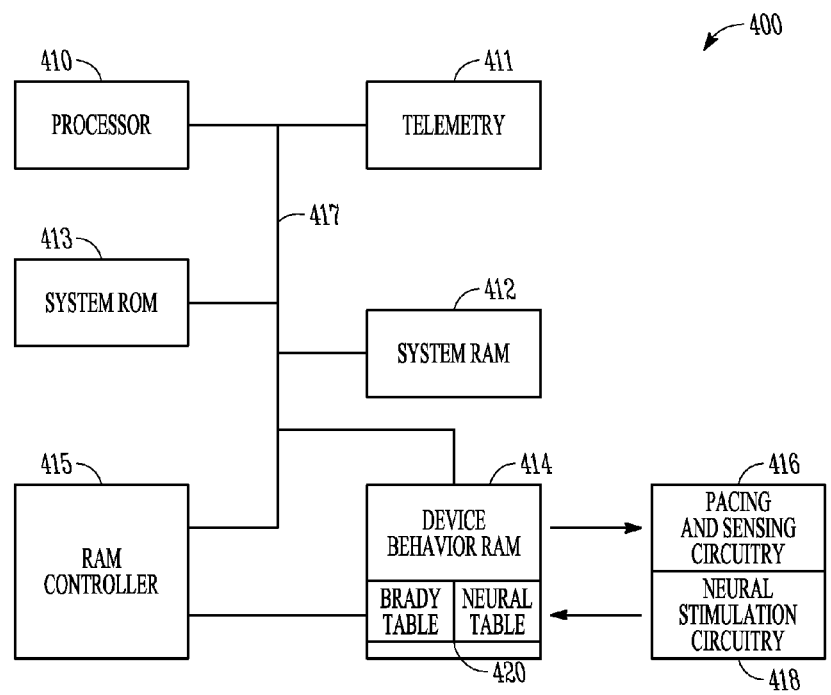
FIG. 9 is a system diagram of a combination implantable neural stimulation device and pacemaker.

7. Example of a Combined Implementation of Neural Stimulator Mode and Brady Pacing According to some examples, the IMD includes multiple device functions such as a combination brady device (e.g., to treat bradyarrhythmia) and neural stimulation device. FIG. 9 shows a block diagram of portions of an example of such an IMD 400 that includes both the brady device circuitry discussed previously as well as the neural stimulator device circuitry. The IMD 400 includes a processor 410, system RAM 412, system ROM 413, data bus 417, and telemetry circuitry 411. The IMD 400 also includes timers including one or more brady event timers and one or more neural event timers. The timers can be implemented in the processor 410 or in one or more separate logic circuits. The IMD 400 includes pacing circuitry 416 and neural stimulation circuitry 418. The IMD 400 includes one or more implantable sensors coupled to sensing circuitry including a sensing channel that generates an electrogram signal representing cardiac electrical activity. The sensing circuitry generates a sensed brady event, such as when an electrogram signal amplitude exceeds a specified threshold.

The IMD 400 includes a device behavior memory that includes a combined brady and neural table 420. In some examples, neural table information is concatenated onto the brady table information to form the combined table in memory. The combined brady and neural table 420 maps one or more particular device states defined by one or more timer states or sensed events to respective device actions. The device actions can include any combination of bradycardia pacing energy delivery, neural stimulation energy delivery, or one or more changes in one or more timer states.

A comparison circuit compares the current state of the IMD 100 to the device states contained in the combined brady and neural table 420. If the current device state matches a particular table device state, the circuitry performs the one or more actions to which the particular table device state is mapped. The combined brady and neural table 420 is accessed by the RAM controller 415 as discussed previously. Device actions may include a neural stimulation energy delivery, a change in state of at least one neural event timer, or both a neural stimulation energy delivery and a change in state of a neural event timer. Device behavior can be changed by loading a different combined brady and neural table 420 or by loading a different neural portion of the table or a different brady portion of the table into the device behavior RAM 414. If a match in the combined brady and neural table 420 is found, the comparison circuit causes performance of one or more associated device actions.

The state of the IMD 400 may be represented by a set of one or more timer outputs, or a set of one or more state register outputs, or a set of one or more sensing circuit outputs, or any combinations of these. The timers include one or more brady event timers and one or more neural event timers. The one or more sensing circuits may be coupled to one or more implantable sensors to indicate an occurrence of any physiologic event of interest to providing bradycardia therapy or to providing neural stimulation therapy. The outputs form a device status word and the current state of the outputs defines the current device status word. The device behavior RAM 414 includes a set of one or more condition words and a set of one or more action words. A condition word represents a particular device state of the combination device. The action words represent respective device actions that include any combination of one or more of neural stimulation energy delivery or bradycardia pacing energy delivery. An action word represents a device action according to which one or more bits of the action word are set or cleared.

Figures 10, 11:
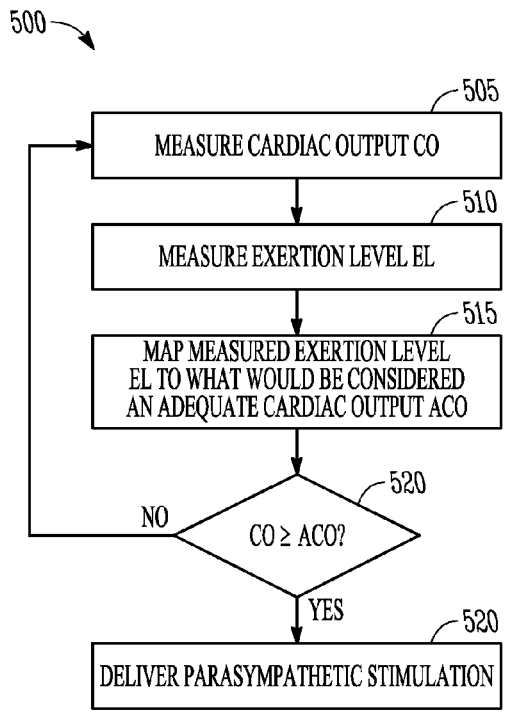
FIG. 10 illustrates an exemplary combination bradycardia pacing mode and neural stimulation mode.
FIG. 11 illustrates an example of action and condition word construction for a combination implantable neural stimulation device and pacemaker.

FIG. 10 illustrates an example of a method 500 for delivering parasympathetic stimulation in conjunction with multisite ventricular pacing as could be implemented by an IMD that is a combination brady device and neural stimulation device. The method can be performed concurrently with the delivery of ventricular resynchronization pacing therapy. Starting at step 505, the device measures an indication of cardiac output (CO). Examples of systems and methods to measure CO are described in the U.S. Pat. Appl. Publ. No. 20050096705 now issued as U.S. Pat. No. 7,657,312, cited previously herein.

The IMD includes an exertion level sensor for measuring an indication of CO. In one example, the exertion level sensor includes a minute ventilation sensor, which includes an exciter and an impedance measuring circuit coupled to a processor. The exciter supplies excitation current of a specified amplitude (e.g., as a pulse waveform with constant amplitude) to excitation electrodes that are disposed in the thorax. Voltage sense electrodes are disposed in a selected region of the thorax so that the potential difference between the electrodes while excitation current is supplied is representative of the transthoracic impedance between the voltage sense electrodes. Processing of the impedance signal allows the derivation of signal representing respiratory activity and/or cardiac blood volume, depending upon the location the voltage sense electrodes in the thorax. If the impedance signal is filtered to remove or attenuate the respiratory component, the result is a signal that is representative of blood volume in the heart at any point in time, thus allowing the computation of stroke volume and, when combined with heart rate, computation of CO. The stroke volume integrated over time (or averaged and multiplied by heart rate) gives an indication of the patient's CO.

At step 510, the patient's exertion level EL is measured. In some examples, the EL is measured using minute ventilation to gauge a patient's breathing. In some examples, the EL is measured using an accelerometer, such that the EL can be implied from measured body acceleration. The device then maps the measured exertion level EL to a cardiac output that would be considered adequate (ACO) for that exertion level, at step 515. At step 520, the measured cardiac output CO is compared with the computed adequate cardiac output ACO. If the measured cardiac output is adequate (e.g., if CO≧ACO plus a possible safety margin), parasympathetic stimulation is delivered to parasympathetic nerves innervating the heart at step 525. Unlike electrostimulation of cardiac tissue, the parasympathetic stimulation does not elicit an immediate evoked response heart contraction. The parasympathetic stimulation allows the patient's ventricular function to be improved without adversely affecting cardiac output.

FIG. 11 shows an example of how the one or more timer states, one or more sensed events, and one or more device actions of the parasympathetic stimulation method illustrated by FIG. 10 can be encoded as one or more condition words and one or more action words. The number of bits shown in the condition word 605 and action word 610 are reduced in this illustrative example to simplify the discussion. Three escape intervals are included: an AVI, a VAI, and a left ventricle pacing interval (LVPI) that starts with a right ventricle sense or pace and upon expiration ends with a left ventricle pace. A sensed event of the measured cardiac output (CO) equaling or exceeding the adequate cardiac output (ACO) plus any safety margin is also included.

Figure 12:
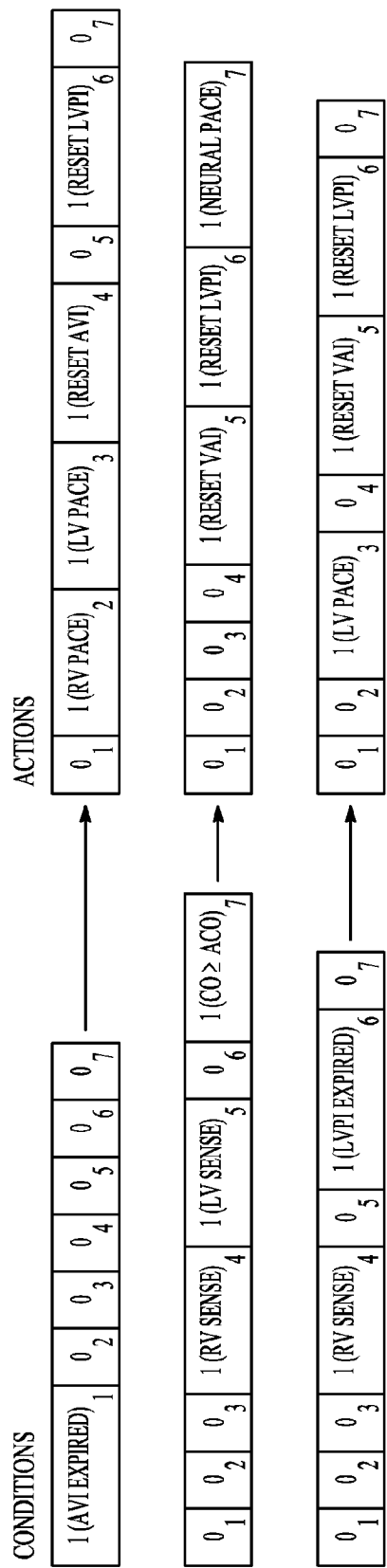
FIG. 12 illustrates exemplary action and condition word pairs for implementing a combination bradycardia pacing mode and neural stimulation therapy mode.

FIG. 12 shows an example of how different condition words may be associated with different action words in a combination brady and neural table in order to implement the method shown in FIG. 10. In this illustrative example, three condition/action word pairs are shown that map different device states to different device actions. Additional pairs are possible. In this example, the first pair shows that a right ventricular pace and a left ventricular pace are delivered if the AVI is expired regardless of what else is included in the current status word. The AVI and the LVPI are reset. CO is less than the ACO, so neural stimulation energy is not delivered. The second pair shows that the VAI timer and the LVPI timer are reset in the event of a right and left ventricle sense. Because the CO is not less than the ACO, neural stimulation energy is delivered. The third pair shows that the left ventricle is paced if the LVPI expires. Because the CO is less than the ACO, neural stimulation energy is not delivered.

8. Method Example of Neural Stimulator Mode Implementation

Figure 13:
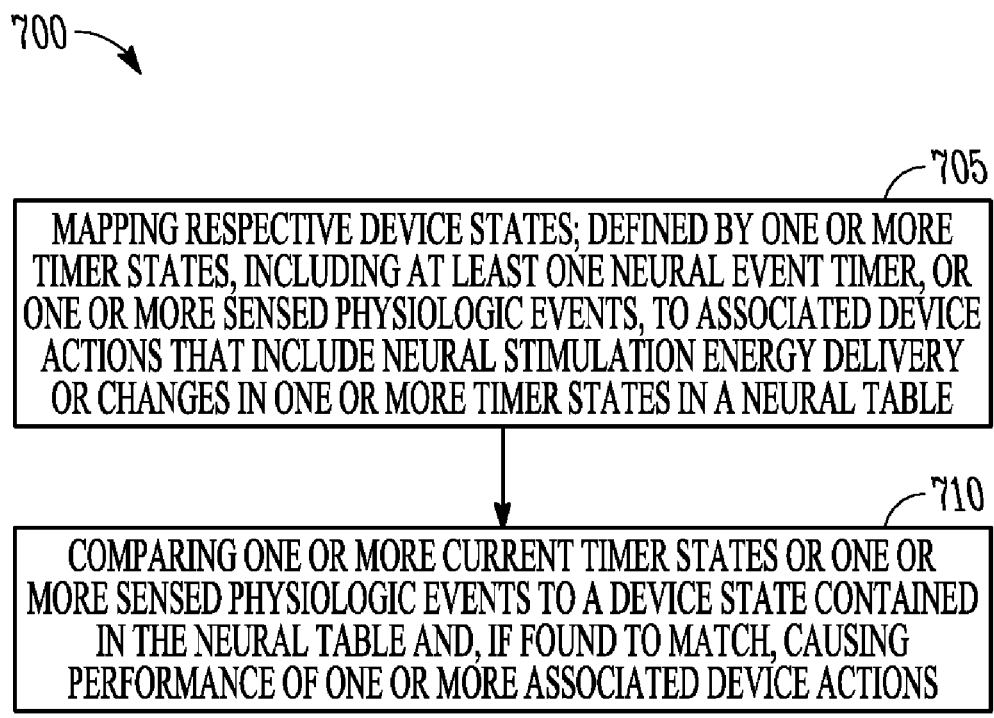
FIG. 13 is an example of a method for implementing a neural stimulation therapy mode.

FIG. 13 is an example of a method 700 for implementing a neural stimulation therapy mode in an IMD. At 705, respective device states are mapped to associated device actions using a neural table. The device states are defined by one or more timer states or one or more sensed physiologic events. The one or more timers include at least one neural event timer. The physiologic events are sensed using one or more implantable sensors. Examples of implantable sensors include a heart sound sensor, a blood pressure sensor, a cardiac signal sensing circuit adapted to sense intracardiac electrograms, a subcutaneous electrocardiograph (ECG) sensing circuit, a cardiac wall motion sensor, a transthoracic impedance sensor, an intracardiac impedance sensor, an accelerometer, and a temperature sensor. The one or more implantable sensors are coupled to sensing circuitry. The sensing circuitry produces an indication of a sensed physiologic event, such as when the electrical sensor signal differs from a specified threshold value by a specified amount. In some examples, the difference is detected using a comparator and the outputs of one or more comparators are included in a device state. One or more of the device actions include delivering neural stimulation energy delivery or changing the state of one or more timers.

In some examples, device states are mapped using respective stored condition words that represent a particular device state according which bits in the word are set or cleared. In some examples, a device status word is formed where the status word includes a set of one or more timer outputs and a set of one or more sensing comparator outputs. The device status word can be mapped bit-by-bit to one or more condition words. In some examples, the method 700 includes detecting a change in device state, such as by detecting a change in one or more bits of the device status word and sequentially comparing one or more condition words with a current device status word when the change in device state is detected.

The condition words are mapped in turn to stored action words. An action word represents a particular device action according to which one or more bits of the word are set or cleared. At 710, one or more current timer states or one or more sensed physiologic events are compared to a device state contained in the neural table. If a match is found, one or more associated device actions are performed. In some examples, an action word is stored in a FIFO queue along with a timestamp when a match is found between the condition word and the current device status word.

In some examples, the method 700 includes implementing brady pacing therapy in an IMD in addition to the neural stimulation therapy. One or more device states are mapped to one or more device actions using a brady table combined with the neural table. The device actions include delivering bradycardia energy therapy or changing a state of one or more timers including one or more brady event timers. One or more current timer states or one or more sensed events are compared to a device state included in the combined brady and neural table. If a match is found, one or more associated device brady and/or neural actions are performed.

Although the embodiments discussed above are in relation to implantable devices that deliver bradycardia therapy, resynchronization therapy, and neural stimulation therapy, the approach of the combination of the firmware, hardware, and the RAM-based behavior table or tables is intended to be flexible enough to be used in any implantable medical device that uses timers and sensor feedback to control electrical stimulation. The timers and sensors may be specific to the intended disease treatment and may change from application to application, but the approach to the core "engine" of the firmware, hardware, and the RAM-based behavior table is the same. In each case, the core engine described herein is capable of producing application-specific therapies by changing the timers and the sensor inputs of the condition words and changing the stimulation output control using action words.

The list of potential disease treatments involving implantable device stimulation of the vagus nerve is quite long and includes the treatment of diseases of the organs innervated by the vagus nerve. Some examples include stimulation of the vagus nerve as part of cardiac therapy such as arrhythmia therapies, heart failure therapies, post-myocardial infarction therapies, angina therapies, and atherosclerosis therapies.

Adding electrical stimulation of other nerves and muscles further expands the list of potential disease treatments. Some examples include nerve stimulation as part of a treatment for inflammatory diseases, and stimulation of the vagus nerve as part of diabetes treatment to affect the pancreas by modulating insulin production. Other examples include treatment of sleep apnea by stimulation of the hypoglossal nerve, the phrenic nerve, or direct muscle stimulation, and treatment of obesity using stimulation of the vagus nerve and/or direct stimulation of stomach muscle. Further examples include neural stimulation to treat pain, epilepsy, or Parkinson's disease.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. A method comprising the acts of:
implementing a neural stimulation therapy mode in an implantable medical device (IMD) comprising stimulation circuitry adapted to provide at least one neural stimulation energy to a patient using at least one neural stimulation electrode, the implementing the neural stimulation therapy mode including:
storing representations of device states as entries of a neural table, wherein a device state is defined by one or more timer states, including at least one neural event timer, or one or more indications of one or more sensed physiologic events;
mapping respective device states to associated device actions in the stored neural table, wherein the device actions include:
one or more of a neural stimulation energy delivery and a change in one or more timer states; and
a set of one or more action inputs, wherein an action input includes at least one of an input to the neural stimulation circuitry and an input to the one or more timers;
detecting a change in a current device state;
searching the neural table entries to identify a match to the current device state in response to the detected change;
applying an action word associated with the identified neural table entry match to action inputs to cause performance of one or more associated device actions, wherein an action input includes at least one of an input to the neural stimulation circuitry and an input to the one or more timers; and
storing an event represented as a device status word and a time stamp in a queue in response to an action input.

2. The method of claim 1, wherein mapping includes:
mapping respective device states to respective stored condition words, the condition words representing a particular device state according to which one or more bits of the word are set or cleared; and
mapping respective condition words to corresponding stored action words that represent corresponding device actions, wherein an action word represents a particular device action according to which one or more bits of the word are set or cleared.

3. The method of claim 2, wherein mapping particular IMD states includes mapping a current device status word bit-by-bit to one or more condition words, and wherein the device status word includes a set of one or more timer outputs and a set of one or more sensing comparator outputs.

4. The method of claim 3, including:
detecting a change in device state by detecting a change in one or more bits of the device status word; and
sequentially comparing one or more condition words with a current device status word when the change in device state is detected.

5. The method of claim 4, wherein storing an event represented as a device status word includes storing an action word in a FIFO queue along with the timestamp when a match is found between the condition word and the current device status word.

6. The method of claim 1, wherein mapping includes:
mapping one or more respective device states to associated device actions in a combined brady and neural table, the device actions include bradycardia energy therapy delivery or one or more changes in one or more timer states; and
comparing one or more current timer states or one or more indications of one or more sensed events to a device state included in the combined brady and neural table and, if found to match, causing performance of one or more associated device actions.

7. The method of claim 1, including sensing one or more physiologic events by detecting when an electrical sensor signal produced by at least one implantable sensor exceeds a specified threshold value, wherein the implantable sensor is selected from the group consisting of:
a) a heart sound sensor;
b) a blood pressure sensor;
c) a cardiac signal sensing circuit adapted to sense intracardiac electrograms;
d) a subcutaneous electrocardiograph (ECG) sensing circuit;
e) a cardiac wall motion sensor;
f) a transthoracic impedance sensor;
g) an intracardiac impedance sensor;
h) an accelerometer; and
i) a temperature sensor.

8. The method of claim 1, wherein mapping device states to device actions in a stored neural table includes mapping device states to device actions in the stored neural table representing timed neural stimulation.

9. The method of claim 1, wherein the IMD includes sensing circuitry adapted to sense exertion of the patient, and wherein mapping device states to device actions in a stored neural table includes mapping device states to device actions in the stored neural table representing neural stimulation in response to a sensed exertion level of the patient.

10. The method of claim 1, wherein mapping device states to device actions in a stored neural table includes mapping device states to device actions in the stored neural table representing neural stimulation energy delivery to one or more of a parasympathetic nerve, a baroreceptors, and a vagus nerve.

11. The method of claim 1, wherein mapping device states to device actions includes mapping a device state, that includes expiration of a neural escape timer, to a device action stored in the stored neural table, wherein the device action includes delivery of neural stimulation energy.

12. The method of claim 1, wherein mapping device states to device actions includes mapping a device state, that includes sensing a physiologic event, to a device action, that includes resetting a neural escape timer.

13. The method of claim 1,
wherein the stimulation circuitry is adapted to provide bradycardia pacing energy;
wherein mapping device states includes mapping respective device states to associated device actions in a combination brady table and neural table; and
wherein comparing the timer states and the indications of events includes comparing the current timer states or the indications of the sensed physiologic events to a device state contained in the combination brady table and neural table.

14. The method of claim 13, wherein the device actions include any combination of bradycardia pacing energy delivery, neural stimulation energy delivery, and one or more changes in one or more timer states.

15. The method of claim 14, wherein mapping device states to device actions includes mapping a device state, that includes expiration of a ventricular pacing interval, to a device action stored in the stored neural table, wherein the device action includes delivery of bradycardia pacing stimulation energy to a ventricle and neural stimulation energy to a parasympathetic nerve.

16. The method of claim 14, wherein mapping device states to device actions includes mapping a device state, that includes expiration of a atrial-ventricular pacing interval (AVI) and a sensed exertion level that exceeds a specified threshold exertion level output, to a device action stored in the stored neural table, wherein the device action includes delivery of bradycardia pacing stimulation energy to a ventricle and neural stimulation energy to a parasympathetic nerve.

17. The method of claim 16, including the mapping the sensed exertion level to a cardiac output, and where in the device state includes expiration of the AVI and a cardiac output that exceeds a specified threshold cardiac output.

18. The method of claim 14, wherein mapping device states to device actions includes mapping a device state, that includes expiration of a left ventricular pacing interval (LVPI) and a sensed exertion level that is less than a specified exertion level output, to a device action stored in the stored neural table, wherein the device action includes delivery of bradycardia pacing stimulation energy to a ventricle and inhibiting neural stimulation energy to a parasympathetic nerve.

19. The method of claim 13, including changing operation of the IMD by loading one or both of a different brady table and a different neural table into a memory of the IMD.

20. A tangible computer readable medium containing device performable instructions which, when performed by a computing device, result in the computing device performing a method comprising the acts of:

storing representations of device states as entries of a neural table, wherein a device state is defined by one or more timer states, including at least one neural event timer, or one or more indications of one or more sensed physiologic events;

mapping respective device states to associated device actions in the stored neural table, wherein the device actions include:

one or more of a neural stimulation energy delivery and a change in one or more timer states; and a set of one or more action inputs, wherein an action input includes at least one of an input to neural stimulation circuitry and an input to the one or more timers, wherein the neural stimulation circuitry is adapted deliver the neural stimulation energy to a patient;

detecting a change in a current device state;

searching the neural table entries to identify a match to the current device state in response to the detected change;

applying an action word associated with the identified neural table entry match to action inputs to cause performance of one or more associated device actions, wherein an action input includes at least one of an input to the neural stimulation circuitry and an input to the one or more timers; and storing an event represented as a device status word and a time stamp in a queue in response to an action input.

* * * * *